United States Patent [19]

Tchen

[11] Patent Number: 4,963,477
[45] Date of Patent: Oct. 16, 1990

[54] PROBE CONTAINING A MODIFIED NUCLEIC ACID, RECOGNIZABLE BY SPECIFIC ANTIBODIES AND USE OF THIS PROBE AND THESES SPECIFIC ANTIBODIES TO DETECT AND CHARACTERIZE A HOMOLOGOUS DNA SEQUENCE

[75] Inventor: Paul Tchen, Nanterre, France

[73] Assignees: Institut National de la Sante et de la Researche Medicale, France; Institut Pasteur, France

[21] Appl. No.: 330,987

[22] Filed: Mar. 28, 1989

Related U.S. Application Data

[63] Continuation of Ser. No. 692,064, Jan. 16, 1985, abandoned.

[30] Foreign Application Priority Data

Jan. 16, 1984 [FR] France .................................. 84 00607

[51] Int. Cl.⁵ ................................................ C12Q 1/68
[52] U.S. Cl. ............................................. 435/6; 435/7; 436/501; 436/800; 436/808; 536/27
[58] Field of Search ................. 536/27; 455/6, 7, 808; 436/501, 810, 808, 800

[56] References Cited

U.S. PATENT DOCUMENTS 4,358,535 11/1982 Falkow et al. ........................ 435/36
4,623,627 11/1986 Huang et al. ........................ 435/6 X

FOREIGN PATENT DOCUMENTS 0128018 12/1284 European Pat. Off. .
83/02286 7/1983 World Int. Prop. O. .

OTHER PUBLICATIONS

Sage et al., FEBS Letters, vol. 108, No. 1, pp. 66–68 (1979).
Broyde, S. et al., Chem–Biol Interactions 47, 1983, pp. 69–78.
Chemical Abstracts 103, No. 13, Sep. 30, 1985, p. 307, abst. No. 101405m, Tchen, P. et al., "Use of Chemically . . . in Hybridization".
Chemical Abstracts 101, No. 7, Aug. 13, 1984, p. 187, abst. No. 49915v, Heller, E. et al., "Comparative Mutagenesis . . . Configuration".
Broyde et al., Chem–Biol. Interactions 47, 1983, pp. 69–78.
Sage et al., FEBS Letters, vol. 18, No. 1, pp. 66–68.

*Primary Examiner*—Amelia B. Yarbrough
*Attorney, Agent, or Firm*—Finnegan, Henderson, Farabow, Garrett & Dunner

[57] ABSTRACT

The invention relates to a kit for detecting the presence of a nucleic acid sequence, such as a gene or a gene fragment, in a composition or a specimen supposed to contain it. The kit comprises a probe containing a nucleic acid complementary with the nucleic acid sequence or gene which is sought. The probe bears at least one 7-iodo-N-2-acetylamino-fluorene group covalently fixed at one at least of the bases of this probe.

12 Claims, No Drawings

PROBE CONTAINING A MODIFIED NUCLEIC ACID, RECOGNIZABLE BY SPECIFIC ANTIBODIES AND USE OF THIS PROBE AND THESES SPECIFIC ANTIBODIES TO DETECT AND CHARACTERIZE A HOMOLOGOUS DNA SEQUENCE

This application is a continuation of application Ser. No. 692,064 filed Jan. 16, 1985 now abandoned.

The invention relates to a probe of high sensitivity containing a modified nucleic acid, and which can be recognized by specific antibodies and to the use of this probe for the detection and characterization of a specific homologous nucleic acid sequence, particularly from a cellular or viral DNA or RNA, in a specimen which can contain it.

The invention relates more particularly, to a probe chemically modified, so that it can, after hybridization with the desired homologous nucleic acid sequence, be detected by antibodies specific with regard to the probe itself.

The invention relates also to a set, outfit or "kit" for the detection and characterization of a cellular or viral, DNA or RNA nucleic acid sequence, which outfit comprises, on the one hand, a probe containing a modified nucleic acid, homologous with the sequence of the modified nucleic acid, homologous with the desired specific nucleic acid, and on the other hand, the antibodies specific with regard to the probe itself, adapted to detect the probe after hybridization of the latter with the desired specific nucleic acid sequence.

The invention finally relates to a process for detecting and characterizing a specific or predetermined sequence of DNA or RNA nucleic acid resorting to the above said probe.

Labelled probes have already been described enabling the detection of a specific nucleic acid sequence, such as a gene or a gene fragment within a composition which can contain it, such probes then containing a DNA sequence consisting of a complementary nucleic acid, which can be hybridized with the desired nucleic acid sequence or gene. The marker is advantageously formed by a modifying group borne by the probe, this modifying group(or so modified DNA) being then recognizable by specific antibodies. For example, the probe is modified by N-acetoxy-N-2-acetylaminofluorene, called below AAF. Such a probe, called below "DNA-AAF probe", which comprises at least one N-2-acetylaminofluorene group fixed covalently at at least one of its, bases has been described in French patent No. 81 24131. It is recognizable by antibodies previously formed against N-2-(guanosine-8-yl)-acetylaminofluorene or against the probe itself bearing acetylaminofluorene residues Such antibodies are called below "anti-AAF antibodies".

The process described in this patent, of detecting the sequence or a desired particular fragment of nucleic acid possibly contained in a given composition consists of contacting the abovesaid composition with a DNA-AAF probe containing the appropriate complementary sequence under conditions such that hybridation takes place between the probe and the desired nucleic acid or sequence or gene, then to reveal the nucleic acid sequence or gene.

The iodine derivative of the AAF has also been fixed, that is to say 7-iodo-N-acetoxy-N-2-acetylaminofluorene, called below AAIF, to the DNA (Fuchs et coll., Biochemistry, vol. 15, 1976, p. 3347 to 3351), in order to study the molecular model obtained at the end of the fixation. However the transposition of this technique to the fabrication of a modified DNA probe which can be recognized by suitable antibodies could not be envisaged until now. In fact, because of the insolubility of the iodine derivative of the N-2-(guanosine-8-yl)-acetylaminofluorene—at least under conditions in which, to the knowledge of the inventors, the latter has been obtainable—, it was not conceivable to produce antibodies against this molecule by immunization of an experimental animal such as the rabbit. In addition, the considerable size at the molecular level of the iodine atom could be considered as opposing a priori the use of groups of this type for the marking of a probe, because of the reduction of the hybridization capacity that could be expected.

These different observations hence were not of a nature to incite the men skilled in the art to turn to AAIF as a marker for the production of detection probes of the above-indicated type. Even without prejudgement which could exist with respect to such a type of marker, there remained to be found means which could permit its easy recognition. Now the present invention resides in the discovery that not only antibodies previously formed against AAF or a DNA-AAF are capable of recognizing the same DNA modified by the AAIF, but also that the sensitivity of detection of this DNA-AAIF by antibodies against AAF was much higher, particularly of the order of ten times, than the detection sensitivity of the DNA-AAF itself by the same antibodies. It is also remarkable that the fixation of "large molecules" to a DNA hardly modified the capacity of the same DNAs, after prior denaturation, of being hybridized with a complementary sequence of a distinct DNA. The sensitivity of detection of by anti-AAF antibodies of a DNA marked by AAF, greater than when the marker is constituted by the AAIF group directly homologous with the antibody, takes on also a particularly important aspect if account is taken of the extremely low concentration condition, even of extreme, dilution, in which operations are obliged to take place, a specific sequence of nucleic acid to be detected in a given biological specimen is often only present in the biological specimen to be studied in infinitesimal amounts and the detection itself is carried out generally under conditions of extreme dilution. For example, when the specific DNA sequence which is sought contains about 3,000 pairs of bases and this sequence belongs to a total gene of haploid cell having about $3 \times 10^{-9}$ pairs of bases, the relative concentration of the specific sequence which is sought in the DNA contained in the biological specimen under study is of about $10^{-6}$. To this extremely low concentration, the extreme effects of dilution of the sequence which is sought, are often added, particularly in prior fractionation tests of the total DNA studied, particularly when this fractionation comprises operations of the electrophoresis type or of a similar type, in order to separate the different homologous species of the DNA put into operation by migrations which are differentiated according to their respective molecular weights, for example in a polyacrylamide agarose gel. If account is taken of the necessarily limited amounts of biological specimen which can thus be fractionated, the multiplication of the detection sensitivity by 10 can become quite essential. In fact, whereas probes which are marked with AAF already enable the detection of amounts of specific sequences of about 10 picograms, the same probe marked with AAIF is suitable for detecting amounts of about 1 picogram.

This set of favorable properties therefore makes AAIF a remarkable marker for nucleic acid probes.

The invention relates to any probe thus formed, more particularly any cloned probe comprising a predetermined sequence of nucleic acid complementary with the sought specific sequence which is inserted in all or part of the nucleic acid of a vector, particularly plasmid or phage which has enabled the realization of cloning by conventional techniques in genetic engineering technology.

Particularly the nucleic acid of the vector which has been used for the cloning was heterologous with respect to the abovesaid predetermined sequence of nucleic acid, that is to say it is of origin different from that of said sequence, that is to say it comes from a different microorganism.

The invention also relates generally to outfits or kits intended for the systematic research of particular nucleotide sequences in a particular biological specimen, and even more generally in any preparations formed in vitro, for example a cDNA resulting from the transcription of an RNA in the presence of suitable desoxyribonucleotides and a reverse transcriptase.

The outfit according to the invention, enabling the detection and the characterization of a sequence or of a particular nucleic acid fragment in a composition which can contain it, comprises:

a probe containing a complementary sequence of the nucleic acid which is sought, said probe comprising at least one AAIF group covalently fixed at one at least of its bases, and anti-AAF antibodies.

Of course the outfit according to the invention can comprise any other elements necessary for its use, particularly reagents for preparing buffer solutions, reagents suitable for extraction if occasion arises of DNAs to be studied from cellular media and, when the abovesaid anti-AAF antibodies are not themselves modified so that they can be directly visualized, antibodies or other distinct polypeptides, themselves capable of reacting with the anti-AAF antibodies and themselves bearers of an easily visualized marker. The visualization can be effected by any suitable means, preferably, the abovesaid second antibodies or corresponding polypeptides are in their turn modified by a fluorescent molecule or by an enzyme, preferably selected from among those to which a substrate corresponds which, when it is modified by the enzyme, gives rise to modifications distinguishable by colorimetric or spectrophotometric means of the absorption by the substrates of one or several particular light radiations.

The method according to the invention is characterized by the fact that there is placed in contact with the composition presumed to contain a sequence or a particular fragment of nucleic acid, under conditions enabling possible hybridization, of a probe containing a complementary nucleic acid which can be hybridized with the nucleic acid sequence or gene which is sought, the probe bearing at least one AAIF group fixed covalently at one at least of its bases and, after possible separation of the non-hybridized probe, the hybridized probe is revealed by placing in contact with anti-AAF antibodies.

Probes according to the invention may contain cellular or viral DNA or RNA specific fragments, or again a particular cDNA fragment.

They can also, particularly within the scope of the process and of the outfit according to the invention be constituted by larger DNA fragments, particularly genome fragments, or even whole genomes of microorganisms, particularly bacterial or viral, marked by AAIF. These probes will then be usable in the tracking down or detection of these microorganisms in any medium capable of containing them.

The DNA-AAIF used as a probe according to the invention is placed in the presence of the DNA under study and the conditions enabling the reappearance of complementary sequences, which can naturally involve a prior denaturation under well-known conditions of the DNAs which can be mutually hybridized.

Advantageously, predetermined amounts of the reaction product are then deposited and fixed under conditions well-known to the specialist, on a cellulose filter or similar support.

As a modification, predetermined amounts of the composition containing the DNA under study are deposited and fixed on such a support prior to the production of hybridization. The latter is then effected directly on the support. After hybridization, the DNA-AAIF not specifically hybridized is removed by rinsing before proceeding to the detection of the hybrids formed, particularly by placing them in the presence of anti-AAF antibodies, which can be fixed to the probe modified and hybridized at the same time with the DNA sequence sought, when the latter is present in the composition used.

After rinsing of the excess antibodies still present, the fixed antibodies can then be either precipitated or detected.

Preferably, the detection is done by means of the distinct antibodies which can react with the anti-AAF antibodies, these separate antibodies then being marked by an enzyme of which it is then possible to detect or measure the activity with respect to a specific substrate. Advantageously, those enzymes will be used which are capable of inducing a colored reaction at the level of the corresponding substrates.

Detection by means of enzymes going colored reactions is very rapid.

The method is very sensitive especially if amplifying systems are used (bands, trees, or balls of antibodies associated with enzymes) so that it permits the localization of the genes after hybridization in situ on the chromosomes, for example, in the case of prenatal diagnosis.

The method may be quantitative by measurement of the intensity of the coloration.

It is also possible, instead and in place of the abovesaid separate antibodies, to use, for example, marked immunoglobulins or protein A of *Staphylococcus aureus* which can be used under similar conditions, also well-known to the technician.

Additional features of the invention will also appear in the course of the description which follows of a typical example of the practising of the process.

Use is made of the following materials and methods.

Phage λ DNAs come Biolabs Inc. (New England).

The ribosomic ribonucleic acid comes from beef liver and the reagents for the demonstration with alkaline phosphatase (RR Fast Blue, Naphtol AS-MX phosphate salt) come from the Sigma Firm.

The nitrocellulose filters, of BA-85 type come from Schleicher and Schüll. The Staph A cells fixed by formalin (marketed under the name Immunoprecipitin) come from Bethesda Research Laboratories.

The "nick-translation" kits (ref. N-5 000) and the α-32 radioactively marked p-dCTP nucleotides, 800 ci/m-mole) come from Amersham.

The AAF and the AAIF are synthesized according to the articles which appear in Biochemistry 15.3 347-3 351 (FUCHS et al.) and Biochemistry. 17. 2 561-2 567 (LEFEVRE et al). They are preserved in tubes wrapped in aluminum foils, under nitrogen at −20° C.

The anti DNA-AAF and anti Guo-AAF antibodies are obtained as described in Febs Lett. 92, 207-210 (LENG et al).). Biochemistry, 18. 1 328-1 332 (SAGE et al) and in Nucleic Acids Res.. 6, 733-744 (GUIGUES et al).

The antibodies bound to peroxidase and alkaline phosphatase come from Miles Laboratories and Institut Pasteur.

The plasmids and M13 clones with the dzeta human globin cellular DNA inserts come from the INSERM U91 unit Henri Mondor Hospital, Creteil, France and from the Department of Medicine of the Yale University of Medicine (New Haven-United States). The 4p7-7 bears a cellular DNA fragment of 464 pairs of dzeta globin bases inserted in the pBR 322 at the Pst 1 site. The same fragment is inserted into the M13 (DNA 1 355-363, COHEN-SOLAL et al).

The monocatenary M13 DNA is prepared according to Messing et al in Nucleic Acids Res.. 9. 309-321.

The PWE6 clone comes from the Centre de Recherches de Biochimie et de Genetiue Cellulaire du CNRS, Toulouse, France. It contains a 45 S mouse ribosomic DNA of 6.6 kilobases inserted in pBR 322 at the EcoRI site (Nucleic Acid Res.. 10, 5 273-5 283. MICHOT et al. and Nucleic Acids Res.. 11, 3 375-3 391, MICHOT et al).

Preparation of the probe (1°) Use of biacatenary nucleic acids

The nucleic acids to be modified are reduced into fragments of about 1,000 pairs of bases (pb) by sonication and dissolved in a sodium citrate buffer (12 mM, pH 7) at a concentration of about 500 μg/ml. After denaturation by heating (100° C., 5 minutes) and rapid cooling in ice, 1/10th of a volume of an AAIF solution in ethanol is added. The total amount of AAIF added must be equal to about 3 times the weight of nucleic acids to be modified. The mixture is incubated 3 hours at 37° C., sheltered from light. After incubation, the excess AAIF is removed by three extractions with cold ethyl ether and preparation is treated with a borate buffer ( 50 mM, pH 9) at 100° C. for 3 minutes, this in order to remove the inter-chain linkages which could have been produced. After neutralization with a Tris HCl buffer (100 mM, pH 7) the preparation is ready for use for the hybridization. It can be preserved at +4° C., or preferably at −20° C., for several years.

When radioactive DNA is used, the "nick-translated" DNA is precipitated with ethanol redissolved in citrate buffer and denatured by heat. Aliquot parts are treated as indicated above omitting the sonication step. The control DNA is treated with pure ethanol. After treatment, EDTA is added to a final molarity of 2 mM and the modified nucleic acids are preserved protected from light at 4° C.

(2°) Use of monocatenary nucleic acids

Procedure is as indicated in (1°) without carrying out a sonication step.

Determination of percentage of modified bases

The percentage of modified bases is determined by measuring the absorption at 310 nm and 260 nm as described in Biochemistry, 11, 2 659-2 666, FUCHS et al and Febs Lett. 34, 295-298 FUCHS et al. When this photometric method cannot be used by reason of specimens being too small, there are deposited on a nitrocellulose filter several dilutions of samples to be tested and a sample already measured. After immunochemical dyeing, the color intensities of the spots are compared.

Hybridization

The tests are done on DNA adsorbed on nitrocellulose filters by current techniques (filtration by means of an apparatus of the "Hybridot" type marketed by Bethesda Research Laboratories or transfer by capillarity by the method of Southern, described in J. Mol. Biol., 98, p. 503, 1975, but the use of other supports can be envisaged (for example nylon filters of the "Biodyne" type marketed by PALL, DBM (diazobenzyloxymethyl) paper (Cell, vol. 5, p. 301, Noyes and Stark, 1975 and Alwine et al. 1977, PNAS, 1974, p. 5 350, Kemp coll.).

The filters are prehybridized for 2 hours at 65° C. in a solution containing:

| | |
|---|---|
| NaCl | 300 mM |
| Sodium citrate, pH 7 | 30 mM |
| Reagent marketed under the name Ficoll 400 by the Pharmacia Fine Chemicals Company | 0.1% |
| polyvinylpyrrolidone 350 | 0.1% |
| glycine | 0.1% |

The hybridization with the modified probe (DNA-AAIF or RNA-AAIF) is done at 65° C. for the desired time in the following solution:

| | |
|---|---|
| NaCl | 300 mM |
| Sodium citrate, pH 7 | 30 mM |
| Ficoll 400 | 0.02% |
| polyvinylpyrrolidone 350 | 0.02% |
| glycine | 0.02% |
| $KH_2PO_4$, pH 7 | 25 mM |
| EDTA, pH 7 | 2 mM |
| sodium dodecylsulfate (SDS) | 0.5% |

The hybridization time depends on the concentration of the probe and the complexity of the sequence which is sought. It can be calculated by known methods. The use of products accelerating the renaturation of the nucleic acids (for example dextran sulfate) or lowering the hybridization temperature (for example formamide) is possible.

After hybridization, the filters are rinsed to remove the excess probe following procedures currently used and described in the literature.

Detection of the probes

The hybridized filters are subjected to the following treatments:

saturation in proteins by incubation for one hour, at room temperature in a solution containing:

| | |
|---|---|
| calf serum | 20% |
| NaCl | 300 nM |
| Na citrate, pH 7 | 30 nM |

| | |
|---|---|
| NP 40 | 1% |

(saturating solution);

Placed in the presence of the first antibody (antibody recognizing the AAIF) for one hour at room temperature. This antibody is diluted with the saturating solution. The dilution ratio depends on the antibody used;

rinsing in a solution containing:

| | |
|---|---|
| NaCl | 300 mM |
| sodium citrate, mH 7 | 30 mM |
| NP 40 | 1% |

(rinsing solution):

incubation for one hour at room temperature with the second antibody, recognizing the first antibody (if the first antibody is a rabbit antibody, the second antibody may be, for example, a rabbit anti IgG antibody bounded to alkaline phosphatase.)

The second antibody is diluted in the saturating solution, in a ratio which depends on the antibody used.

rinsing by using the same rinsing solution as that indicated above;

development of second antibody by known techniques (for example colored enzymatic reaction of the alkaline phosphatase).

Sensitivity of the method

The tests were done by using as a target viral DNA (λ phage) or human genes (foetal dzeta globin, 460 pb) or mouse (ribosomic DNA 6.6 kb) cloned in bacterial plasmids (pBR 322) and as bicatenary DNA probe (DNA of λ phage or pBR 322 plasmid), monocatenary (M13 phage DNA bearing a 464 pb insert of human dzeta globin), or RNA (beef ribosomic RNA).

For the detection of the probes, the first antibody was a rabbit anti-guanosine-AAF antibody (crude serum) at a dilution of 1/200 and the second antibody, a rabbit anti-IgG antibody bonded to alkaline phosphatase and used at a dilution of 1/400.

Under these conditions, the sensitivities obtained were as follows;

for bicatenary DNA probes used at a concentration higher than or equal to 500 ng/ml ($500 \times 10^{-9}$ g/ml): sensitivity better than 2 pg of target DNA ($2 \times 10^{-12}$ g);

for monocatenary DNA probes used at a concentration higher than or equal to 100 ng/ml: sensitivity better than 2 pg of target DNA;

for ribosomic RNA probes at a concentration of 200 ng/ml: sensitivity in the neighborhood of 200 pg.

It is recalled that a sensitivity of 2 pg of a target DNA corresponds to the detection of a gene of 1,000 pb in 7 μg of total human DNA. This sensitivity is of the same order of magnitude as that required for prenatal diagnosis of falciform anemia.

Comparison of the respective sensitivities of DNA-AAF and DNA-AAIF probes

Ribo- or deoxyribonucleic acids react easily in vitro at a pH with AAF and AAIF. Under the above described conditions, the derivatives are linked principally to the carbon 8 of the guanine residue by a covalent linkage. The antibodies obtained by immunizing rabbits with a DNA-AAF and Guo-AAF specifically recognize DNA modified by AAF. They recognize also DNA and RNA modified by AAIF. Results of table I below show a larger amount of DNA found in a precipitate when DNA is modified by AAIF.

Small amounts of normal DNA are precipitated by anti-DNA-AAF antibodies. To differentiate the modified or unmodified DNA, anti-Guo-AAF antibodies are preferably used since the results obtained are better. In fact, only negligible amounts of unmodified DNA are precipitated by purified anti-Guo-AAF antibodies. This permits the use of the probes for the separation of specific gene sequences from complex mixtures.

The detection of the modified nucleic acids by nucleic chemical techniques is done in the following manner. The modified DNA is bonded to the nitrocellulose filters and the filters are then treated as indicated above. Considering that the number of parameters to be studied is very large, small round filters, 25 mm in diameter are chosen since they are easy to manipulate. By using DNA modified by AAIF (5% modified base), the sensitivity limit is less than 1 pg when the second antibodies are linked to alkaline phosphatase and about 8 pg when they are linked to peroxidase.

As regards the DNA fusion temperature, it is approximately reduced by 1.1° C. and 0.4° C. respectively for 1% of base modified by AAF and AAIF (Biochemistry, 15, 3 347–3 351, FUCHS and coll.: Febs Lett., 34, 295–298, FUCHS et coll.; Biochemistry, 6, 117–182, KRIEK et coll.; Biochem. Biophys. Acta, 232, 436–450, KAPULER et coll.).

Hybridizations by spots were done to evaluate the effect of modifications of the AAF and of the AAIF on bicatenary DNA probes. Nitrocellulose filters with three DNA spots of PBR 322 (422 pg, 2 ng, 20 ng) and one spot of DNA (1 ng) were hybridized with radioactive DNA probes, either unmodified, or with about 5M of base modified by AAF or AAIF. After hybridization, given groups of filters were washed with more or less vigor, dried and auto-radiographed for 8 hours. No non-specific hybridization could be observed, even with the gentlest washing (NaCl/sodium citrate, 15 minutes at room temperature).

The stability of the hybrid is tested on filters with DNA spots (10 pg, 100 pg, 1 ng, 10 ng) which are washed with different forces after hybridization:

either with radioactive modified DNA probes;
or with controlled probes.

At each degree of washing force, a group of filters was dried and they were auto-radiographed. No appreciable difference could be seen between the three probes. No spot was observed on the filters hybridized with a control DNA probe whatever the washing force. The spot corresponding to 10 ng is slightly visible on the filter hybridized with a probe modified with AAF. With a probe modified with AAIF, the corresponding spot at 1 ng is also visible.

For each of the above-indicated experiments, each of the probe concentrations was 2 ng/ml, the specific activity was $5 \times 10^7$ cpm/μg and the auto-radiograph time was 18 hours. Under these conditions, the sensitivity of detection obtained with the probes modified by AAF and AAIF are about 1/100 and 1/10 compared with that obtained by autoradiography.

Considering that any type of nucleic acid can be modified either by AAF or AAIF, the possibility has been tested of using M13 monocatenary probes and immunocleic RNA probes in hybridization experiments. For hybridization with monocatenary M13 DNA, each filter contains a DNA control spot of phage λ and decreasing amounts of DNA of plasmid 4p7-7. The monocatenary DNA of M 13 recombinant phage with the same insert of 464 pairs of bases of dzeta globine is modified by AAF or AAIF (5% of pairs of modified bases). Several concentrations of a probe of 125 to 1 500 ng/ml were tested. Hybridization and washing were carried out at 65° C. In this case, the concentration of the hybridizable sequences of the probe was about 33 ng/ml and the target sequences on the spots were comprised between 660 and 5 ng. All the spots were colored except the negative control. The coloration of the spots is more intense with the probe modified by AAIF.

Similar tests were done with RNA probes modified by AAIF.

The liver ribosomic RNA (Sigma, reference R 5 502) is dissolved in citrate buffer (2 mM, pH 6.7) sonicated briefly to reduce its size to fragments of about 1000 bases and modified by AAIF. Spots were formed with the DNA of pBR 322 (100 ng) to have a negative control, and decreasing amounts of DNA of pWE6, a recombinant plasmid with a ribosomic 45 S mouse DNA insert of 6.6 kb. The amount of sequences hybridizable on the spots is comprised between 30 ng and 230 pg. Different probe concentrations were used ranging from 200 to 2300 ng/ml. Only slight differences in the intensities of coloration were observed with higher probe concentrations. When immunonucleic probes are used in high concentrations, the background noise of the filters remains very low. The possibility of using high concentrations of probe is interesting when it is desired to make short hybridizations.

From all these results, it appears that the properties of the nucleic acids modified by AAIF renders them suitable for the detection of specific sequences.

The use of the iodized AAIF derivative in place of AAF contributes a ten fold gain in sensitivity.

In addition, when the second antibodies used are bonded to alkaline phosphatase, the sensitivity is in the field of picogram.

The invention is obviously not limited to the embodiments described above by way of example and technicians skilled in the art can introduce therein modifications without however departing from the scope of the following claims.

By way of modifications usable at the level of the detection of the hybrids formed with the probe according to the invention, is mentioned:

the development (by radioactivity) of the hybrids formed, by example by means of the use of anti-DNA-AAF antibodies rendered radio-active by iodine 125 or 131 or radio-active protein A, which will be fixed to the antibodies.

Finally, by way of modifications of possible uses, will be mentioned the application of the probe according to the invention to the purification of complementary DNA contained in an initial composition, particularly by means:

of protein A associated with a solid support (for example constituted by agarose beads);

precipitating antibodies associated or not with a solid support (agarose or latex beads, etc.); to ensure the selective precipitation of the hybrid formed.

The invention naturally thus extends its effects to any probe marked by modified groups, equivalent to the N-2-acetylamino-7-iodofluorene groups whose formula is recalled below:

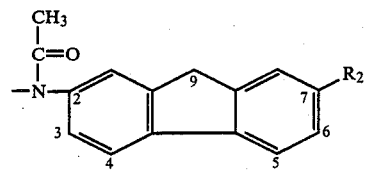

In particular, equivalents of these marker groups are constituted by any groups in which the iodine atom at the 7 position is replaced by another atom or substituent group of several atoms, which, like iodine renders impossible the insertion of the fluorene nucleus which is then associated with it between two pairs of bases. Such a substituent group is for example constituted by an alkyl radical, particularly methyl or preferably tert-butyl. A peptide group can also be envisaged. Substitution on the fluorene nucleus can also possibly take place on another position of the nucleus, for example at the 9 position; this amounts, for example, to double methylation of the 9 position.

The introduction of other substituent groups on the fluorene groups or the modification of the fluorene groups by substituents which do not modify the essential immunogenic properties, can only lead to the constitution of equivalents, when the thus modified DNA probes are still recognized by antibodies previously formed against N-2-(guanosine)-8-yl)acetylaminofluorene or against molecules resulting from modifications of the latter group. These modifications must not however spoil their solubility in aqueous solutions, to the extent necessary for the production of antibodies against this latter type of molecule. In known manner this immunization is generally produced after coupling of the molecule concerned with a carrier molecule contributing to the reinforcement of its immunogenicity, for example a serum albumin. By way of other examples of modifications which cannot spoil the solubility, will be mentioned, for example, replacement of the N-2-acetyl group by an N-2-formyl group or N-2-propionyl group in the N-2-(guanosine-8-yl)-2-acetylaminofluorene.

TABLE I

| | PERCENTAGES OF IMMUNOPRECIPITATED DNA | | |
|---|---|---|---|
| Antibodies | DNA (control) | DNA-AAF (~5% modified bases) | DNA-AAIF (~5% modified bases) |
| Rabbit (normal serum) | <0.1 | <0.1 | <0.1 |
| Anti-Guo-AAF (whole serum) | 0.2 | 44.7 | 81.9 |
| Anti-Guo-AAF (purified) | 0.1 | 41.5 | 71.9 |
| Anti-DNA-AAF (purified) | 1.0 | 66.8 | 93.6 |

I claim:

1. A kit for the detection or isolation of a first predetermined nucleotide sequence, comprising:
   a probe containing a second nucleotide sequence which is complementary to said first predetermined nucleotide sequence and which can be hybridized with said first predetermined nucleotide sequence;
   said probe further containing a 7-iodo-N-2-acetylaminofluorene group covalently fixed to a base of said second complementary nucleotide sequence; and first antibodies formed against N-2-(guanosine-8-yl)acetylaminofluorene or against a nucleotide sequence convalently fixed to an N-2-acetylaminofluorene group.

2. The kit of claim 1, which further comprises means for visualizing said first antibodies.

3. The kit of claim 2, wherein said visualizing means comprise second antibodies or polypeptides which are capable of reacting with said first antibodies and which bear a marker.

4. The kit of claim 3, wherein said marker is an enzyme or a fluorescent molecule.

5. The kit of claim 1, wherein said first and second nucleotide sequences are DNA sequences.

6. A kit for the detection or isolation of a first predetermined nucleotide sequence, comprising:
   a probe containing a second nucleotide sequence which is complementary to said first predetermined nucleotide sequence and which can be hybridized with said first predetermined nucleotide sequence;
   said probe further containing a 7-iodo-N-acetoxy-N-2-acetylaminofluorene group covalently fixed to a base of said second complementary nucleotide sequence;
   first antibodies formed against N-2-(guanosine-8-yl)-acetylaminofluorene or against a nucleotide sequence convalently fixed to an N-2-acetylaminofluorene group; and
   means for visualizing said first antibodies.

7. The kit of claim 6, wherein said visualizing means comprise second antibodies or polypeptides, which are capable of with said first antibodies and which bear a marker.

8. The kit of claim 7, wherein said first and second nucleotide sequences are DNA sequences.

9. A method for detecting a first predetermined nucleotide sequence in a biological medium, comprising:
   contacting said medium, under hybridization conditions, with a prove containing a second nucleotide sequence which is complementary to said first predetermined nucleotide sequence and which can be hybridized with said first predetermined nucleotide sequence, said probe further containing a 7-iodo-N-2-acetylaminofluorene group covalently fixed to a base of said second complementary nucleotide sequence, to hybridize said probe to said first predetermined nucleotide sequence; and then
   contacting said hybridized probe and first predetermined nucleotide sequence with first antibodies formed against N-2-(guanosine-8yl)-acetylaminofluorene or against of nucleotide sequence covalently fixed to an N-2-acetylaminofluorene group.

10. The method of claim 9, which further comprises visualizing said first antibodies by reacting said first antibodies with a labeled antibody or labeled polypeptide to said first antibodies.

11. The method of claim 9, wherein the 7-iodo-N-2-acetylaminofluorene group is 7-iodo-N-acetoxy-N-2-acetylaminofluorene.

12. The method of claim 11, wherein the first antibodies are antibodies that immunologically recognize N-2-(guanosine-8-yl)-acetylaminofluorene.

* * * * *

UNITED STATES PATENT AND TRADEMARK OFFICE
CERTIFICATE OF CORRECTION

PATENT NO. : 4,963,477

DATED : October 16, 1990

INVENTOR(S) : Paul Tchen

It is certified that error appears in the above-identified patent and that said Letters Patent is hereby corrected as shown below:

<u>Claim 1</u>, col. 10, line 62, change "containing" to --that comprises--;

line 66, delete ";";

line 67, change "said probe further containing" to --and--.

col. 11, line 4, "yl)" should be followed by -- - -- (a hyphen).

<u>Claim 6</u>, col. 11, line 18, "sequence" should be followed by --as claimed in claim 1--; "," should be followed by --further--; and ":" should be deleted;

lines 19-31 should be deleted in their entireties.

UNITED STATES PATENT AND TRADEMARK OFFICE
CERTIFICATE OF CORRECTION

PATENT NO. : 4,963,477

DATED : October 16, 1990

INVENTOR(S) : Paul Tchen

It is certified that error appears in the above-identified patent and that said Letters Patent is hereby corrected as shown below:

<u>Claim 7</u>, col. 12, line 3, "of" should be followed by --reacting--.

<u>Claim 9</u>, col. 12, line 9, after "said" insert --first predetermined nucleotide sequence in the biological--;

line 10, "prove containing" should be --probe comprising--;

line 14, "containing" should be --comprising--.

Signed and Sealed this

Second Day of June, 1992

Attest:

DOUGLAS B. COMER

Attesting Officer

Acting Commissioner of Patents and Trademarks